(12) United States Patent
Sekiguchi

(10) Patent No.: US 9,066,650 B2
(45) Date of Patent: Jun. 30, 2015

(54) MEDICAL CONTROL SYSTEM

(71) Applicant: OLYMPUS MEDICAL SYSTEMS CORP., Tokyo (JP)

(72) Inventor: Kiyoshi Sekiguchi, Tokyo (JP)

(73) Assignee: OLYMPUS MEDICAL SYSTEMS CORP., Tokyo (JP)

( * ) Notice: Subject to any disclaimer, the term of this patent is extended or adjusted under 35 U.S.C. 154(b) by 0 days.

(21) Appl. No.: 14/176,855

(22) Filed: Feb. 10, 2014

(65) Prior Publication Data

US 2014/0192176 A1 Jul. 10, 2014

Related U.S. Application Data

(63) Continuation of application No. PCT/JP2013/066956, filed on Jun. 20, 2013.

(30) Foreign Application Priority Data

Aug. 7, 2012 (JP) .................................. 2012-174914

(51) Int. Cl.
*A61B 1/00* (2006.01)
*H04N 7/18* (2006.01)
*G06F 3/041* (2006.01)

(52) U.S. Cl.
CPC ......... *A61B 1/00006* (2013.01); *A61B 1/00114* (2013.01); *A61B 1/00124* (2013.01); *G06F 3/041* (2013.01); *H04N 7/181* (2013.01)

(58) Field of Classification Search
CPC ........... A61B 1/00006; A61B 1/00114; A61B 1/00124; G06F 3/041; H04N 7/181
USPC ............... 348/64, 65, 72, 211.99, 211.14, 74, 348/143, 220; 600/417, 429, 109, 921, 118, 600/160
See application file for complete search history.

(56) References Cited

U.S. PATENT DOCUMENTS

| 6,858,004 | B1 | 2/2005 | Ozawa et al. | |
|---|---|---|---|---|
| 8,634,942 | B2* | 1/2014 | Hong et al. | 700/83 |
| 2007/0120550 | A1* | 5/2007 | Miyake et al. | 323/911 |

(Continued)

FOREIGN PATENT DOCUMENTS

| JP | A-2002-010974 | 1/2002 |
|---|---|---|
| JP | A-2003-190084 | 7/2003 |
| JP | A-2007-082630 | 4/2007 |
| JP | A-2009-183686 | 8/2009 |

OTHER PUBLICATIONS

Jul. 16, 2013 International Search Report issued in International Patent Application No. PCT/JP2013/066956 (with English translation).

(Continued)

*Primary Examiner* — Behrooz Senfi
(74) *Attorney, Agent, or Firm* — Oliff PLC

(57) ABSTRACT

A medical control system comprises: first and second controllers; a touch panel operation unit which receives an operation to the controllers; a switching unit which selectively switches a connection state between first and second states. The operation unit has a touch signal transmission unit which transmits a signal to the first controller when and the operation unit is touched in the first state. The first controller has a first operation command transmission unit which transmits to a peripheral equipment an command in which an operation content of the peripheral equipment is specified by the signal, a first connection state detection unit which detects a change of connection state from the first state to the second state by the switching unit during a period the operation unit is being touched, a first control unit which stops a transmission of the command in accordance with a detection result of the detection unit.

6 Claims, 10 Drawing Sheets

(56) References Cited

U.S. PATENT DOCUMENTS

2009/0199121 A1* 8/2009 Sekiguchi et al. ............ 715/771
2009/0276515 A1* 11/2009 Thomas et al. ............... 709/223
2012/0274586 A1* 11/2012 Southworth et al. .......... 345/173

OTHER PUBLICATIONS

Jul. 16, 2013 Written Opinion issued in International Patent Application No. PCT/JP2013/066956 (with English translation).

* cited by examiner

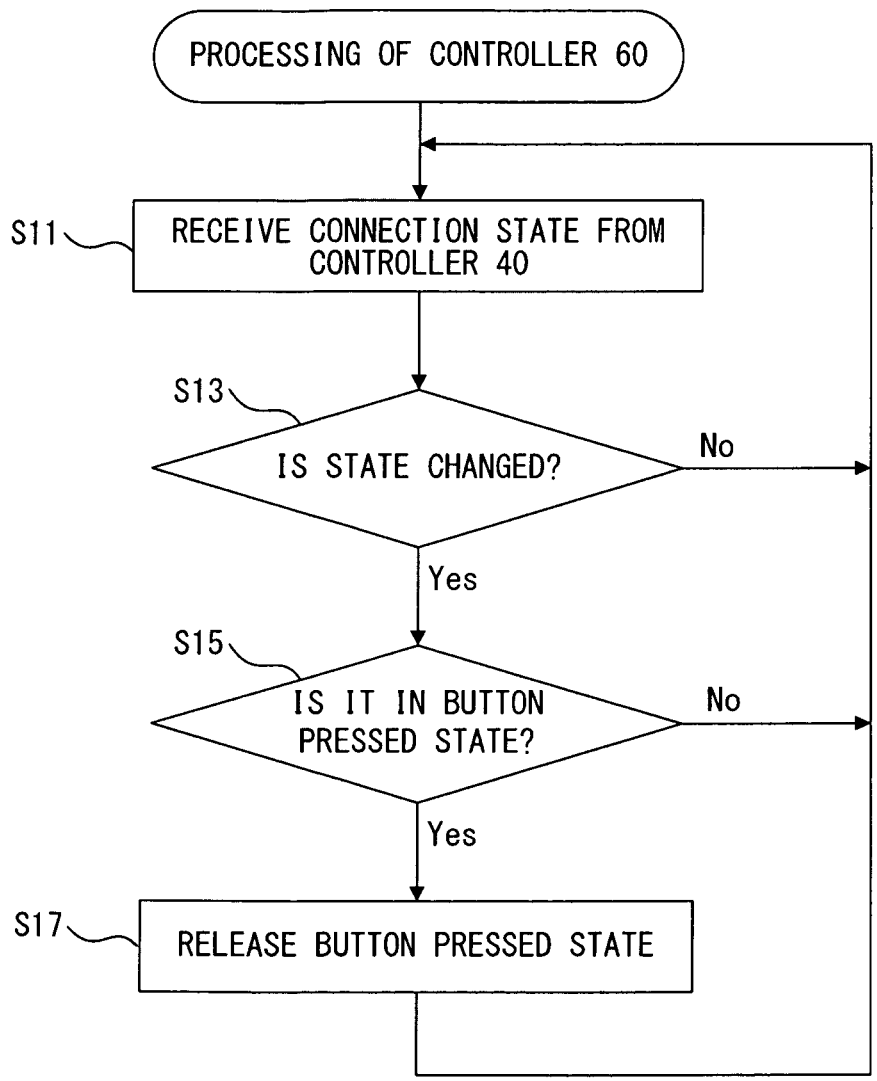
F I G. 4

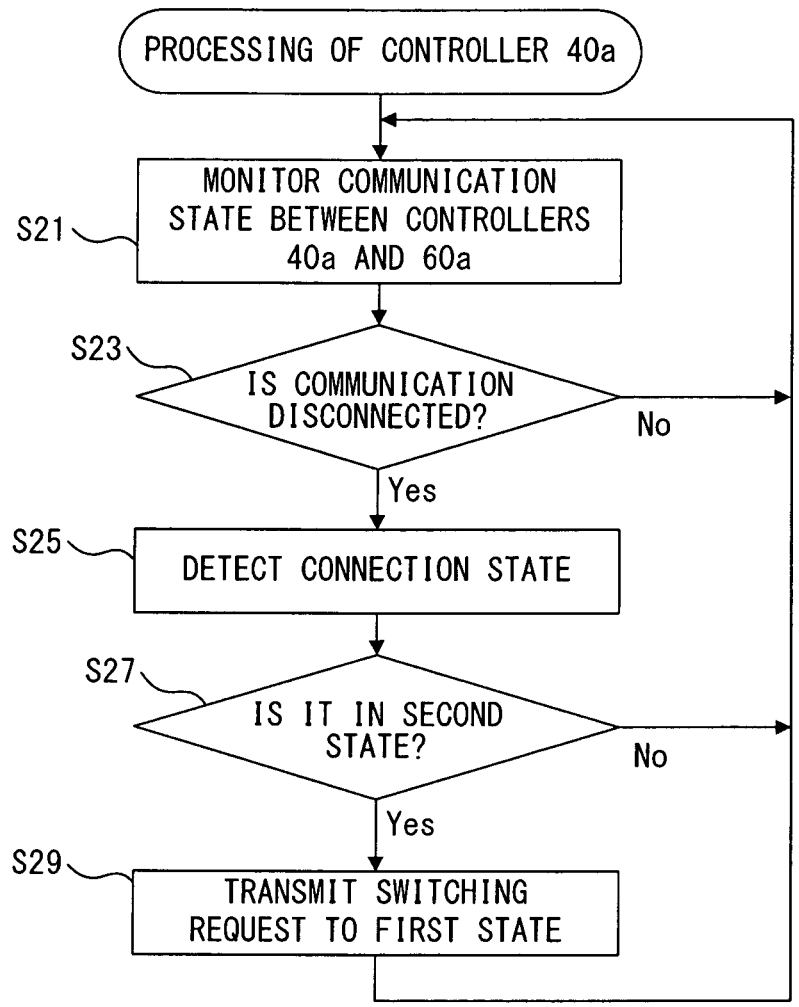
F I G. 8

MEDICAL CONTROL SYSTEM

CROSS-REFERENCE TO RELATED APPLICATIONS

This application is based upon and claims the benefit of priority of the prior Japanese Patent Application No. 2012-174914, filed Aug. 7, 2012, the entire contents of which are incorporated herein by reference.

This is a Continuation Application of PCT Application No. PCT/JP2013/066956, filed Jun. 20, 2013, which was not published under PCT Article 21(2) in English.

BACKGROUND OF THE INVENTION

1. Field of the Invention

The present invention relates to a medical control system, and in particular, it relates to a medical control system for selectively controlling a plurality of controllers.

2. Description of the Related Art

A technology is known which selectively operates a plurality of devices from one operation means by using a switching device. For example, Japanese Laid-open Patent Publication No. 2002-010974 discloses an electronic endoscopy system which includes two scopes that are connected to different processors. In the electronic endoscopy system disclosed in Japanese Laid-open Patent Publication No. 2002-010974, an instruction may be entered from a keyboard to a scope connected to a processor that was selected by the switching device. By using such a technology, various advantages may be obtained including improvements in operation efficiencies and the like, since operation means need not be provided for each operation target.

SUMMARY OF THE INVENTION

One aspect of the present invention provides a medical control system including: a first controller and a second controller each of which is configured to control different peripheral equipment; a touch panel operation unit configured to receive an operation to the first controller and the second controller; a switching unit configured to selectively switch a connection state between a first state in which the first controller receives an operation from the touch panel operation unit and a second state in which the second controller receives an operation from the touch panel operation unit; wherein the touch panel operation unit has a touch signal transmission unit which transmits a touch signal to the first controller when the connection state is the first state and the touch panel operation unit is touched, and the first controller has a first operation command transmission unit which transmits to the peripheral equipment an operation command in which an operation content of the peripheral equipment is specified by the received touch signal, a first connection state detection unit which detects a change of a connection state from the first state to the second state by the switching unit during a time period that the touch panel operation unit is being touched, and a first control unit which stops a transmission of the operation command in accordance with a detection result of the first connection state detection unit.

BRIEF DESCRIPTION OF THE DRAWINGS

The present invention will be more apparent from the following detailed description when the accompanying drawings are referenced.

FIG. 4 is a flowchart which illustrates processing performed at a second controller according to embodiment 1 of the present invention.

FIG. 8 is a flowchart which illustrates processing performed at a first controller according to embodiment 2 of the present invention.

DESCRIPTION OF THE PREFERRED EMBODIMENT

In reality, there are various operation means other than keyboards, and recently, such operation means as a touch panel display which consists of a display and a touch panel sensor disposed so as to overlap with the display have been widely used.

A touch panel display is configured such that it outputs a signal at a time of starting contact with the touch panel display and at a time of completing contact with the touch panel display. Accordingly, a controller which has received a signal (hereafter indicated as a touch signal) output from the touch panel display at the time of a start of contact usually judges that the contact with the touch panel sensor is being continued until the controller receives a signal (hereafter indicated as a touch completion signal) output at the time of a completion of contact.

In this case, when a switching of a connection destination by a switching device occurs during the time period starting from a contact start to a contact completion, a controller which has received a touch signal judges that the contact is being continued even after a contact has been completed, since it has never received a touch completion signal even though a contact has been completed, and continues processing. Such a phenomenon is known as a so-called sticking phenomenon.

Embodiment 1

Figure 1:
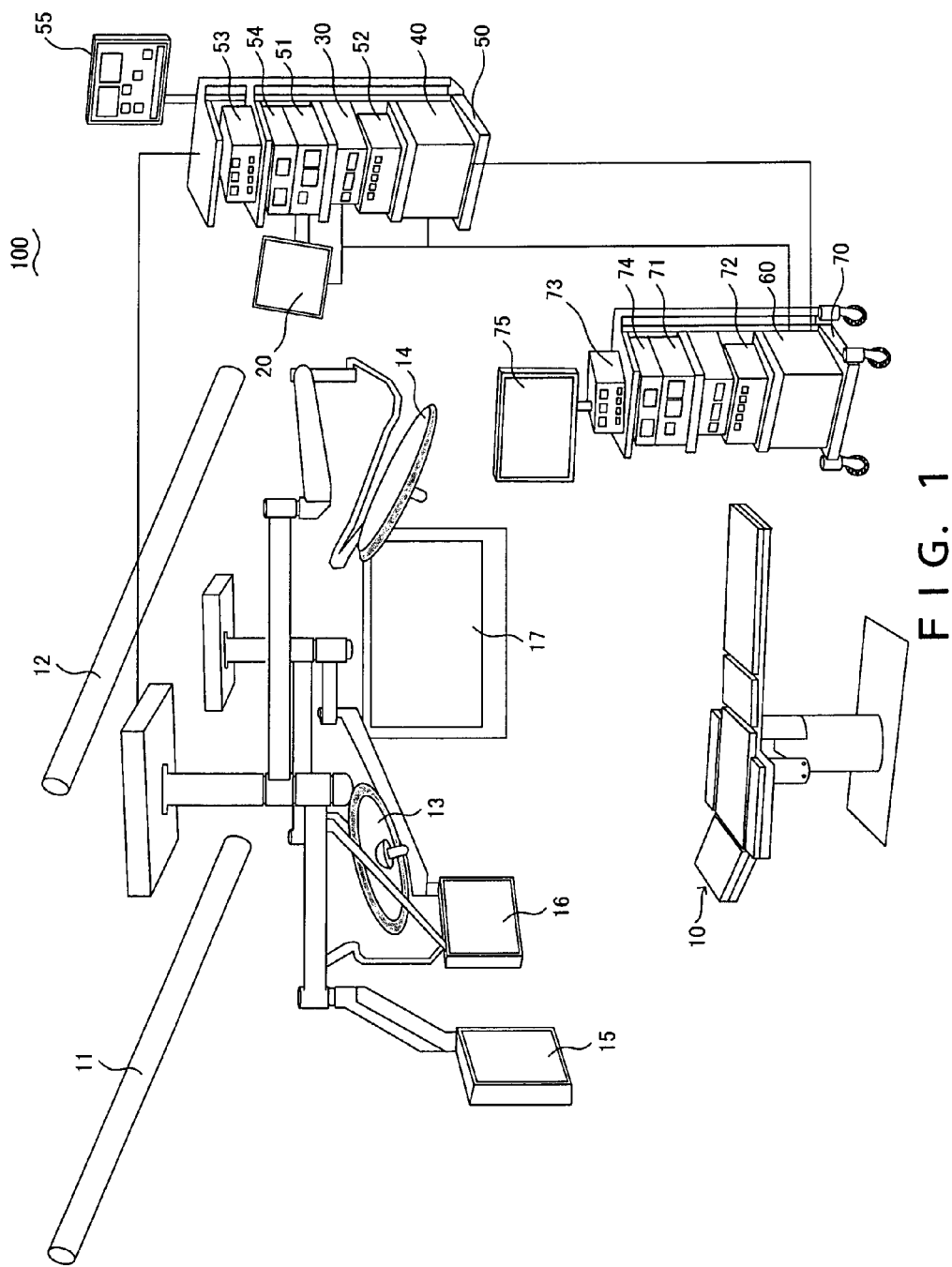
FIG. 1 is a configuration diagram of an entirety of a medical control system according to embodiment 1 of the present invention.

FIG. 1 is a configuration diagram of an entire medical control system according to the present embodiment. A medical control system 100 illustrated in FIG. 1 includes a controller 40 and a controller 60 which respectively control different peripheral equipment, an operation panel 20 which receives an operation to a controller 40 and a controller 60, a switching device 30 which switches a connection state between an operation panel 20 and controllers (a controller 40 and a controller 60), and a plurality of peripheral equipment controlled by a controller 40 or a controller 60.

Peripheral equipment controlled by a controller 40 which is a first controller of a medical control system 100 includes such medial equipment as a light source device 51, an electric scalpel device 52, an insufflator 53, a processor 54 to which an endoscope is connected, and a monitor 55, and the like, for example, which are installed in a rack 50. The controller 40 further controls equipment permanently installed in an operating room such as a patient's bed 10 on which a patient lies down, ceiling lightings (a ceiling lighting 11, a ceiling lighting 12), shadowless lamps (a shadowless lamp 13, a shadowless lamp 14) suspended from a ceiling, and a plurality of monitors (a monitor 15, a monitor 16, and a monitor 17) suspended from a ceiling and displaying medical images and the like, as peripheral equipment.

Peripheral equipment controlled by a controller 60 which is a second controller of a medical control system 100 includes such medial equipment as a light source device 71, an electric scalpel device 72, an insufflator 73, a processor 74 to which an endoscope is connected, and a monitor 75 and the like, for example, which are installed in a cart 70.

The medical control system 100 may further include various devices and equipment that are not illustrated in FIG. 1. The medical control system 100 may include an operative field camera which observes operative fields, and a video recorder which stores images generated by a processor 54 or a processor 74, and the like, and these may be controlled by a controller 40 or a controller 60.

An operation panel 20 is an operation unit which receives an operation to a controller 40 and a controller 60. An operation panel 20 is a touch panel display, for example, being configured such that a liquid-crystal display which is a display unit and a touch panel sensor which is a sensor unit disposed to overlap with the liquid-crystal display are integrated. By operating a controller 40 or a controller 60 via an operation panel 20, peripheral equipment which is a controlled device connected to the controller 40 or the controller 60 may be controlled. An operation panel 20 is operated by a nurse who is in a non-sterilize area, and usually a surgeon does not directly operate the operation panel 20.

A switching device 30 is a switching unit for selectively switching a connection state between a first state in which an operation panel 20 and a controller 40 are electrically connected and a second state in which an operation panel 20 and a controller 60 are electrically connected. While the controller 40 is operated by an operation received by the operation panel 20 when a connection state is a first state, the controller 60 is operated by an operation received by the operation panel 20 when a connection state is a second state. That is to say, a switching device 30 plays a role of switching a controller as an operation target.

Although a medical control system 100 provided in an operation room where endoscopic surgeries are performed is illustrated in FIG. 1, a use of the medical control system 100 is not limited to endoscopic surgeries, but the medical control system 100 may be used for other operations or diagnoses. In addition, the medical control system 100 may be provided in such rooms as examination rooms other than operation rooms. Further, although a switching device 30 and a controller 40 are separately configured, the switching device 30 and the controller 40 may be integrally configured.

Figure 2:
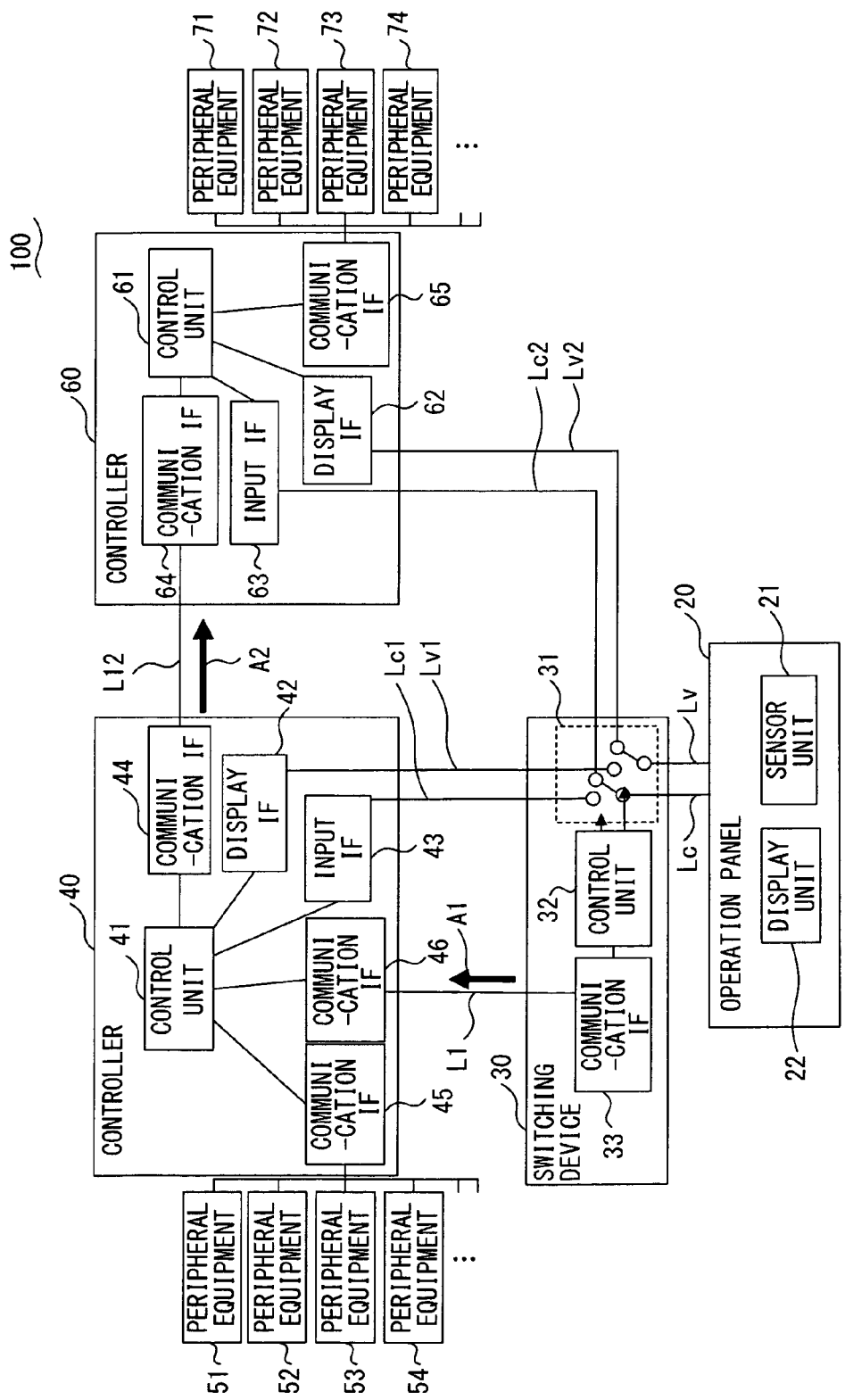
FIG. 2 is a diagram explaining the main components of a medical control system according to embodiment 1 of the present invention.

FIG. 2 is a diagram for explaining the main components of a medical control system according to the present embodiment. Hereafter, in reference to FIG. 2, detailed explanations are given for an operation panel 20, a switching device 30, a controller 40, and a controller 60 that are main components of a medical control system 100.

As illustrated in FIG. 2, an operation panel 20 and a switching device 30 are electrically connected by a coordinate signal line Lc and a video signal line Lv, and a switching device 30 and a controller 60 are electrically connected by a coordinate signal line Lc2 and a video signal line Lv2. A switching device 30 and a controller 40 are electrically connected by a control signal line L1 as well, in addition to a coordinate signal line Lc1 and a video signal line Lv1. Further, a controller 40 and a controller 60 are electrically connected to each other by a control signal line L12.

An operation panel 20 includes a display unit 22 which displays an image in accordance with a video signal which was received through a video signal line Lv and a sensor unit 21 which is disposed so as to overlap with a display unit 22. A sensor unit 21 is configured to detect a touch operation on a display unit 22 and to output an operation signal to a coordinate signal line Lc. In further detail, the sensor unit 21 outputs, to a coordinate signal line Lc, a touch signal that includes coordinate information of a position on which it was touched at the time of starting the touch operation, and outputs, to a coordinate signal line Lc, a touch completion signal at the time of completing (releasing) the touch operation.

A switching device 30 includes a switching unit 31 which switches a connection state between a first state and a second state, a control unit 32 which controls a switching unit 31 in response to a switching request, and a communication interface unit (hereafter indicated as a communication IF unit) 33 for communicating with a controller 40.

A switching unit 31 further includes a first switch for switching a connection destination of a coordinate signal line Lc between a coordinate signal line Lc1 and a coordinate signal line Lc2 and a second switch for switching a connection destination of a video signal line Lv between a video signal line Lv1 and a video signal line Lv2. A first switch and a second switch are configured to interlock with each other. Specifically, when a connection destination of the coordinate signal line Lc is switched to a coordinate signal line Lc1, a connection destination of the video signal line Lv is switched to a video signal line Lv1, and when a connection destination of the coordinate signal line Lc is switched to a coordinate signal line Lc2, a connection destination of the video signal line Lv is switched to a video signal line Lv2. With this, a switching device 30 has a connection state of either a first state in which an operation panel 20 and a controller 40 are electrically connected or a second state in which an operation panel 20 and a controller 60 are electrically connected.

Although in essence a control unit 32 controls a switching unit 31 in response to a switching request, it also controls a switching unit 31 for switching a connection state when a controller 40 is shut down, in addition to when it receives the switching request. In further detail, when a connection state is a first state, and when a communication IF unit 33 detects a shutdown of a controller 40 through a control signal line L1, a control unit 32 controls a switching unit 31 and switches a connection state to a second state. Further, when a connection state is a first state, and when a control unit 32 detects that a video signal transmitted from a controller 40 through a video signal line Lv1 has stopped (cable disconnections or the like), a control unit 32 controls a switching unit 31 and switches a connection state to a second state. Similarly to the above, when a connection state is a second state, and when a control unit 32 detects that a video signal transmitted from a controller 60 through a video signal line Lv2 has stopped, a control unit 32 controls a switching unit 31 and switches a connection state to a first state.

A communication IF unit 33 mainly plays a role of receiving a switching request from a controller 40 through a control signal line L1 and of reporting to a controller 40 a connection state through a control signal line L1. A connection state may be reported either spontaneously by a communication IF unit 33 or in response to a request from a controller 40.

A controller 40 includes a control unit 41 which controls an operation of an entire controller 40, a display IF unit 42 for outputting a video signal to an operation panel 20, an input IF unit 43 for receiving operation signals (a touch signal, a touch completion signal) from the operation panel 20, a communication IF unit 44 for communicating with a controller 60, a communication IF unit 45 for communicating with peripheral equipment (a light source device 51, an electric scalpel device 52, an insufflator 53, a processor 54, and the like), and a communication IF unit 46 for communicating with a switching device 30.

A communication IF unit 44 mainly plays a role of receiving a switching request from a controller 60 through a control signal line L12 and of reporting to a controller 60 a connection state reported from a switching device 30 through a control signal line L12. Further, a communication IF unit 46 mainly plays a role of transmitting a switching request to a switching device 30 through a control signal line L1 and of receiving a connection state from a switching device 30 through a control signal line L1. A switching request transmitted by a communication IF unit 46 is a switching request generated by a controller 40 or a switching request generated by a controller 60.

A controller 60 includes a control unit 61 which controls an operation of an entire controller 60, a display IF unit 62 for outputting a video signal to an operation panel 20, an input IF unit 63 for receiving operation signals (a touch signal, a touch completion signal) from an operation panel 20, a communication IF unit 64 for communicating with a controller 40, and a communication IF unit 65 for communicating with peripheral equipment (a light source device 71, an electric scalpel device 72, an insufflator 73, a processor 74, and the like). That is to say, a controller 60 is configured similarly to a controller 40 except that the controller 60 does not have a configuration which corresponds to a communication IF unit 46 of the controller 40.

A communication IF unit 64 mainly plays a role of transmitting a switching request to a controller 40 through a control signal line L12 and of receiving a connection state from a controller 40 through a control signal line L12.

In a medical control system 100 configured as mentioned above, an operation signal and a video signal are exchanged between an operation panel 20 and a controller 40 in a first state in which a coordinate signal line Lc and a coordinate signal line Lc1 are electrically connected, and in which a video signal line Lv and a video signal line Lv1 are electrically connected. An operation signal and a video signal are exchanged between an operation panel 20 and a controller 60 in a second state in which a coordinate signal line Lc and a coordinate signal line Lc2 are electrically connected, and in which a video signal line Lv and a video signal line Lv2 are electrically connected.

Accordingly, in a first state, an image in accordance with a video signal generated by a controller 40 is displayed on an operation panel 20 (a display unit 22), and a controller 40 controls peripheral equipment in accordance with an operation to a controller 40 received by the operation panel 20 (a sensor unit 21). Similarly, in a second state, an image in accordance with a video signal generated by a controller 60 is displayed on an operation panel 20, and a controller 60 controls peripheral equipment in accordance with an operation to a controller 60 received by the operation panel 20.

Figure 3:
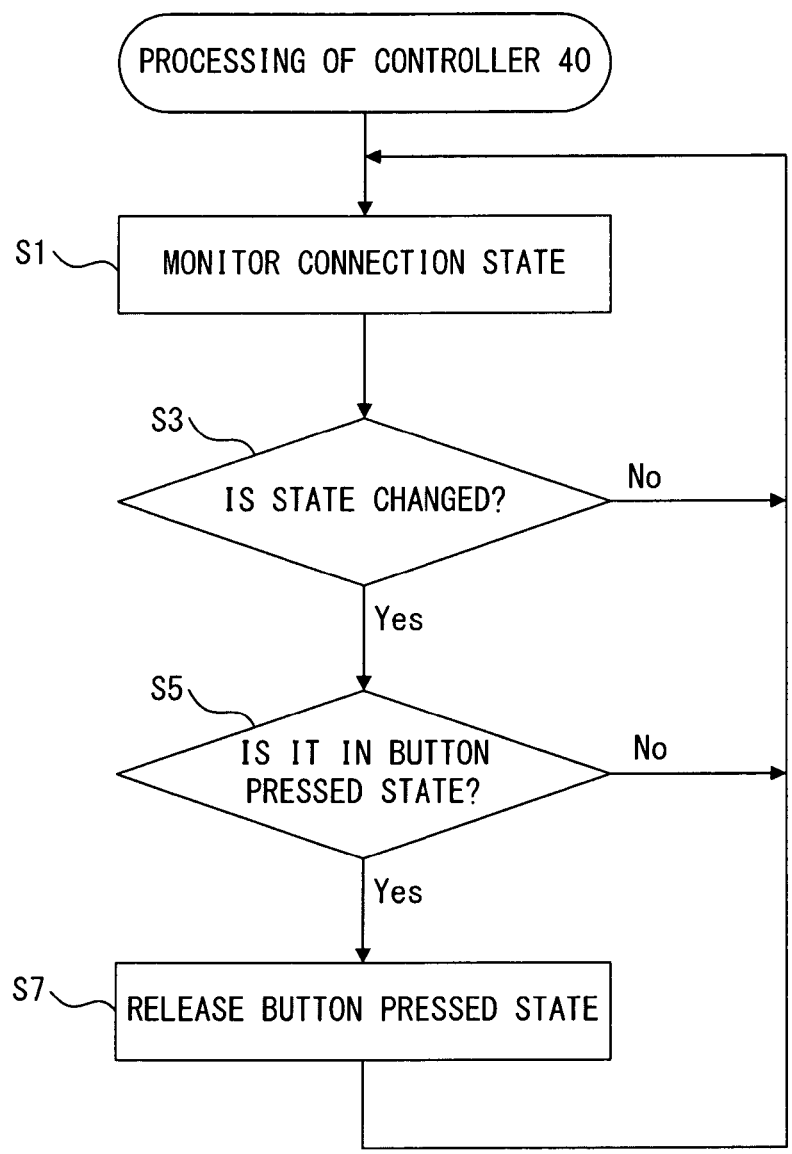
FIG. 3 is a flowchart which illustrates processing performed at a first controller according to embodiment 1 of the present invention.

Further, in a medical control system 100, a controller 40 executes the processing illustrated in FIG. 3, in addition to control processing of peripheral equipment that is executed in accordance with an operation upon receiving an operation signal. That is to say, a controller 40 monitors a connection state reported through a control signal line L1 which is illustrated by arrow A1 of FIG. 2 (step S1), and judges whether or not a change has occurred in a connection state (step S3). When a controller 40 judges that a change has occurred in a connection state, it further judges whether or not a state is a button pressed state (a state in which a controller 40 is executing a control of peripheral equipment which corresponds to pressing a button of a display unit 22) (step S5). When a controller 40 judges that a state is a button pressed state, it stops a control which corresponds to pressing a button and releases a button pressed state (step S7). Then, it goes back to step S1 and monitors a connection state. Further, when a controller 40 judges that no change has occurred in a connection state or when it judges that a state is not a button pressed state, it goes back to step S1 and monitors a connection state.

Further, in a medical control system 100, a controller 60 executes the processing illustrated in FIG. 4, in addition to control processing of peripheral equipment that is executed in accordance with an operation upon receiving an operation signal. A controller 60 monitors a connection state reported through a control signal line L12 which is illustrated by arrow A2 of FIG. 2 (step S11), and judges whether or not a change has occurred in a connection state (step S13). When a controller 60 judges that a change has occurred in a connection state, it further judges whether or not a state is a button pressed state (a state in which a controller 60 is executing a control of peripheral equipment which corresponds to pressing a button of a display unit 22) (step S15). When a controller 60 judges that a state is a button pressed state, it stops a control which corresponds to pressing a button and releases a button pressed state (step S17). Then, it goes back to step S11 and monitors a connection state. Further, when a controller 60 judges that no change has occurred to a connection state or when it judges that a state is not a button pressed state, it goes back to step S11 and monitors a connection state.

Hereafter, explanations are given for an operation of a medical control system 100 when a switching of a connection state of a switching device 30 has occurred during a touch operation (that is, a time period starting from a touch operation start until a touch operation completion).

Figure 5:
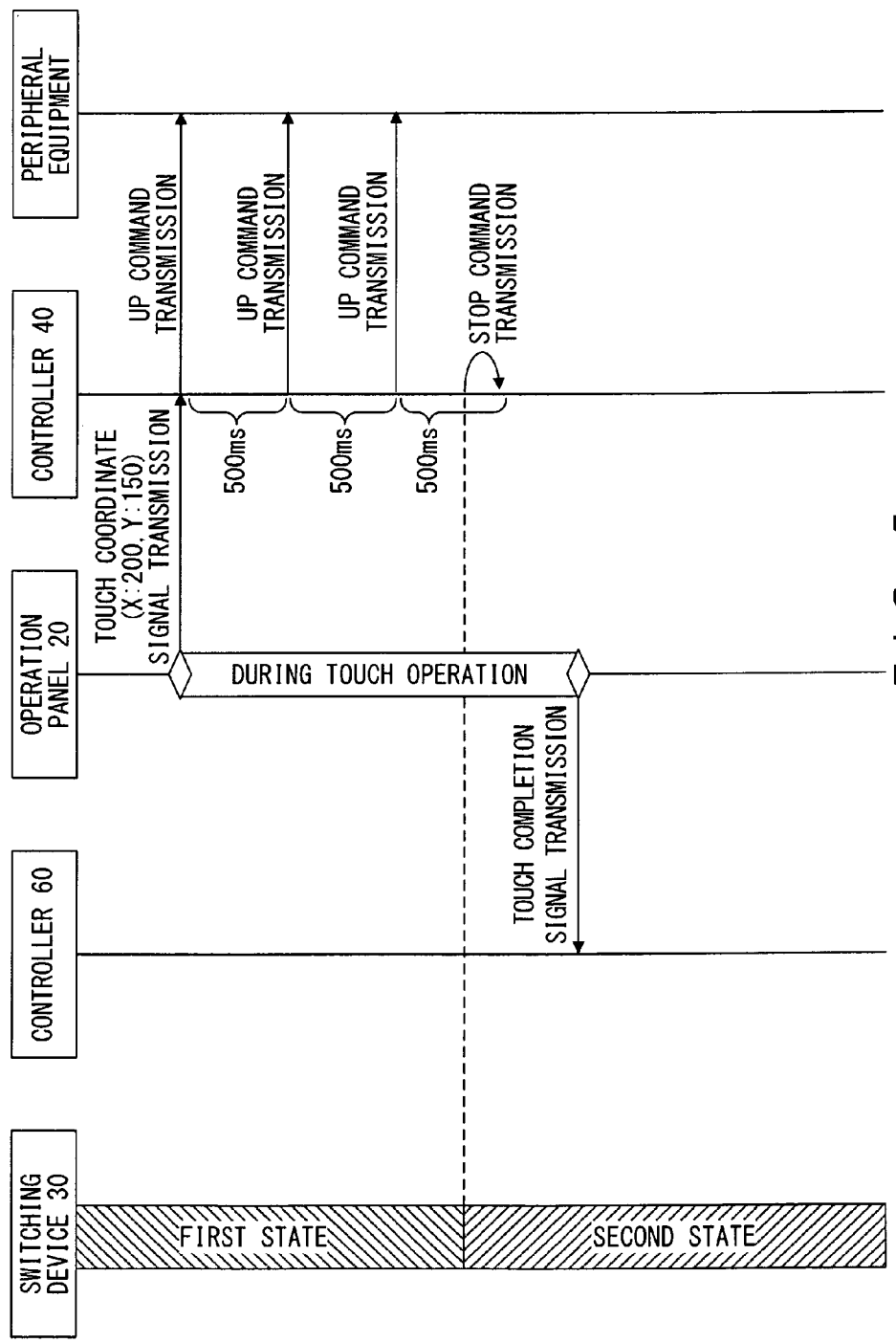
FIG. 5 is a sequential diagram which illustrates a flow of a signal between main components of a medical control system according to embodiment 1 of the present invention during a touch operation.

First, in reference to FIG. 5, explanations are given for a case in which a connection state has been switched to a second state during a touch operation in a first state. Such a switching of a connection state may occur in the following situations. First is a case in which a controller 40 transmits a switching request to a switching device 30, as a result of a switching button displayed on a display unit 22 being pressed during a touch operation in a first state. Second is a case in which a controller 40 transmits a switching request to a switching device 30, as a result of an error or an alert occurring in a controller 40 during a touch operation in a first state. Further is a case in which a controller 60 is started up in a state where a controller 60 is connected more preferentially than a controller 40. In this case, a started-up controller 60 transmits a switching request to a switching device 30 via a controller 40. A switching of a connection state may also occur when a switching device 30 detects that a controller 40 has been shut down, or when a video signal line Lv1 has been disconnected.

When a touch operation to an operation panel 20 is started in a first state, an operation panel 20 transmits, to a controller 40, a touch signal which includes a touch coordinate. A controller 40 which has received a touch signal specifies a content of an operation by the touch coordinate and controls peripheral equipment in accordance with the content of the operation. For example, when a button to increase an output of an electric scalpel device 52 is displayed in a touch coordinate (X, Y)=(200, 150) included in a received touch signal, a controller 40, upon a receipt of the touch signal, transmits, on a regular basis (every 500 ms, for example) an UP command that instructs an electric scalpel device 52 to increase an output. After that, when the connection state is changed from a first state to a second state during the touch operation, a controller 40 detects a change in a connection state from a first state to a second state by processing illustrated in FIG. 3 and stops transmitting an UP command. Finally, when the touch operation is completed in a second state, the operation panel 20 transmits a touch completion signal to a controller 60.

In a conventional controller, a regular transmission of an UP command is performed until a touch completion signal is received. On the other hand, a controller 40 stops transmitting an UP command when it detects a switching of a connection state, even when a touch completion signal is not received, and the controller 40 is different from a conventional controller in this respect.

Figure 6:
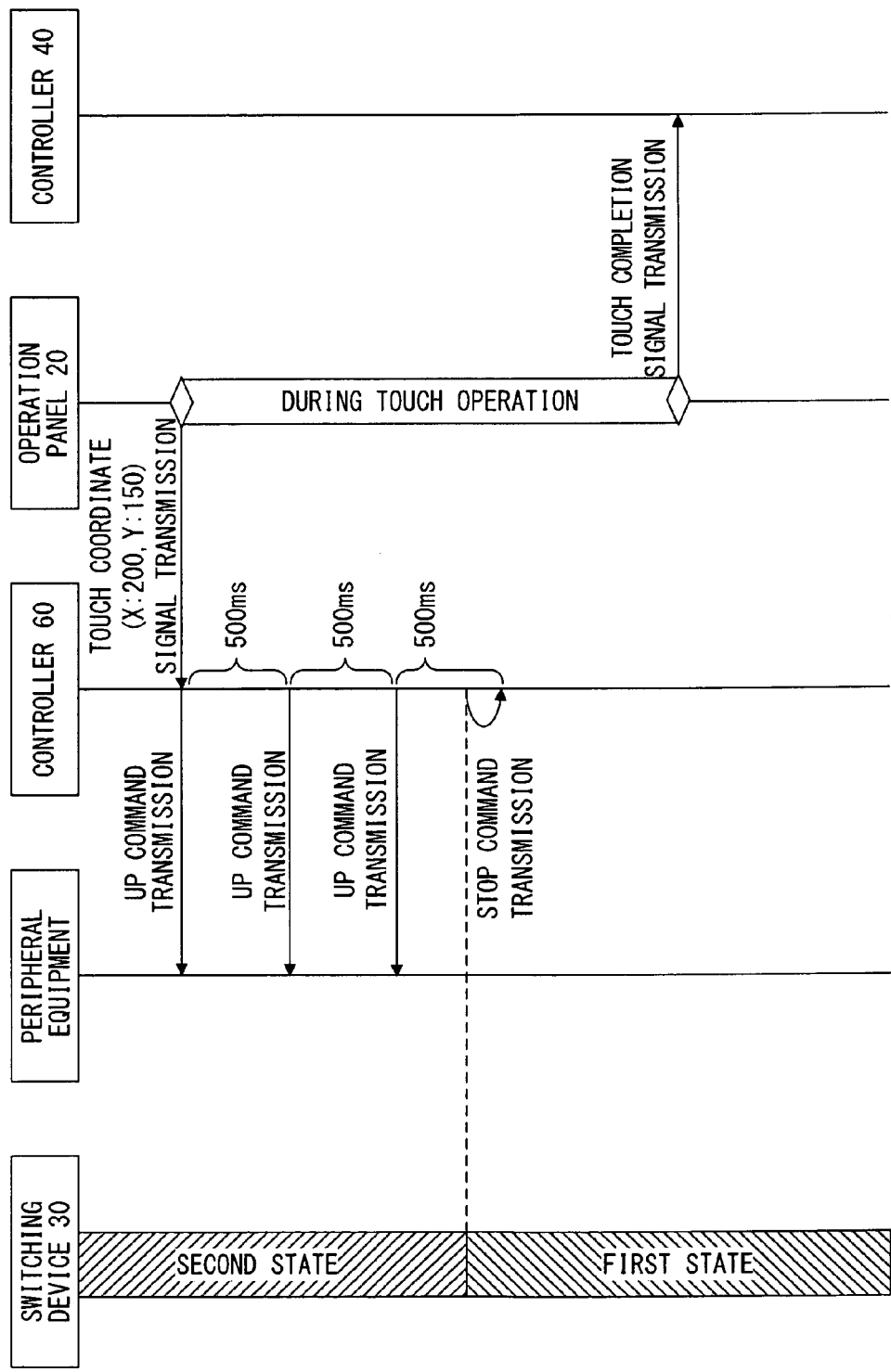
FIG. 6 is another sequential diagram which illustrates a flow of a signal between main components of a medical control system according to embodiment 1 of the present invention during a touch operation.

Next, in reference to FIG. 6, explanations are given for a case in which a connection state has been switched to a first state during a touch operation in a second state. Such a switching of a connection state may occur in the following situations. First is a case in which a controller 60 transmits a switching request to a switching device 30 via a controller 40, as a result of a switching button displayed on a display unit 22 being pressed during a touch operation in a second state. Second is a case in which a controller 60 transmits a switching request to a switching device 30 via a controller 40, as a result of an error or an alert occurring in a controller 60 during a touch operation in a second state. Further is a case in which a controller 40 is started up and transmits a switching request to a switching device 30 in a state where a controller 40 is connected more preferentially than a controller 60. A switching of a connection state may also occur when a video signal line Lv2 has been disconnected.

When a touch operation to an operation panel 20 is started in a second state, an operation panel 20 transmits, to a controller 60, a touch signal which includes a touch coordinate. A controller 60 which has received a touch signal specifies a content of an operation by a touch coordinate and controls peripheral equipment in accordance with the content of the operation. For example, when a button to increase an output of an electric scalpel device 72 is displayed in a touch coordinate (X, Y)=(200, 150) included in a received touch signal, a controller 60, upon a receipt of the touch signal, transmits, on a regular basis (every 500 ms, for example) an UP command that instructs an electric scalpel device 72 to increase an output. After that, when a connection state is changed from a second state to a first state during a touch operation, a controller 60 detects a change in a connection state from a second state to a first state by processing illustrated in FIG. 4 and stops transmitting an UP command. Finally, when a touch operation is completed in a first state, the operation panel 20 transmits a touch completion signal to a controller 40.

Similarly to a controller 40, a controller 60 is different from a conventional controller in that it stops transmitting an UP command when it detects a switching of a connection state, even when a touch completion signal is not received.

As mentioned above, in a medical control system 100 according to the present embodiment, since each controller monitors a connection state of a switching device 30, when a connection state of a switching device 30 is changed during a touch operation, a control that is being executed by a controller, in accordance with a touch operation received by an operation panel 20, is released. Accordingly, a so-called sticking phenomenon can be prevented, and as a result of this, inconveniences which may occur due to a switching by a switching device 30 can be avoided.

Embodiment 2

Figure 7:
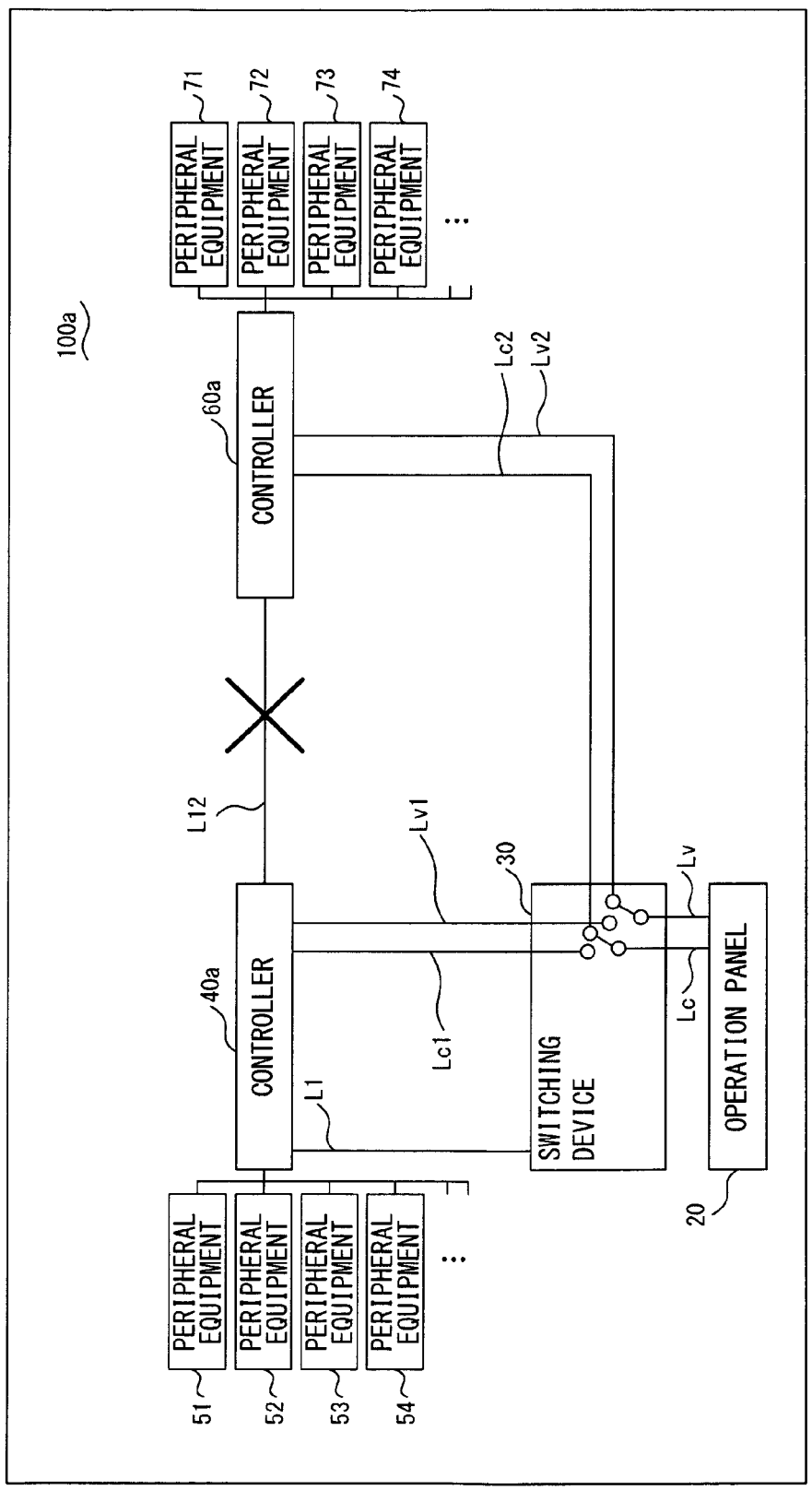
FIG. 7 is a diagram for explaining main components of a medical control system according to embodiment 2 of the present invention.

FIG. 7 is a diagram for explaining the main components of a medical control system according to the present embodiment. A medical control system 100*a* according to the present embodiment, which is illustrated in FIG. 7, is similar to a medical control system 100 according to the first embodiment, which is illustrated in FIG. 2, except that a controller 40*a* and a controller 60*a* are included instead of a controller 40 and a controller 60. A controller 40*a* and a controller 60*a* are similar to a controller 40 and a controller 60 illustrated in FIG. 2, except that a controller 40*a* and a controller 60*a* monitor a communication between a controller 40*a* and a controller 60*a*. Accordingly, detailed explanations for a configuration of a medical control system 100*a* are omitted.

A controller 40*a* according to the present embodiment executes processing illustrated in FIG. 8, in addition to control processing of peripheral equipment that is executed in accordance with an operation upon receiving an operation signal and processing illustrated in FIG. 3. That is to say, a controller 40*a* monitors a communication state between a controller 40*a* and a controller 60*a* through a control signal line L12 (step S21), and judges whether or not a communication state is a disconnection state (step S23). When a controller 40*a* judges that a communication state is a disconnection state, it further detects a connection state reported through a control signal line L1 (step S25) and judges whether or not a connection state is a second state (step S27). When a controller 40*a* judges that a connection state is a second state, it transmits, to a switching device 30, a switching request which requests a switch to a first state (step S29). Then, it goes back to step S21 and monitors a communication state. Further, when a controller 40*a* judges that a communication state is normal or when it judges that a connection is not in a second state, it goes back to step S21 and monitors a communication state.

Figure 9:
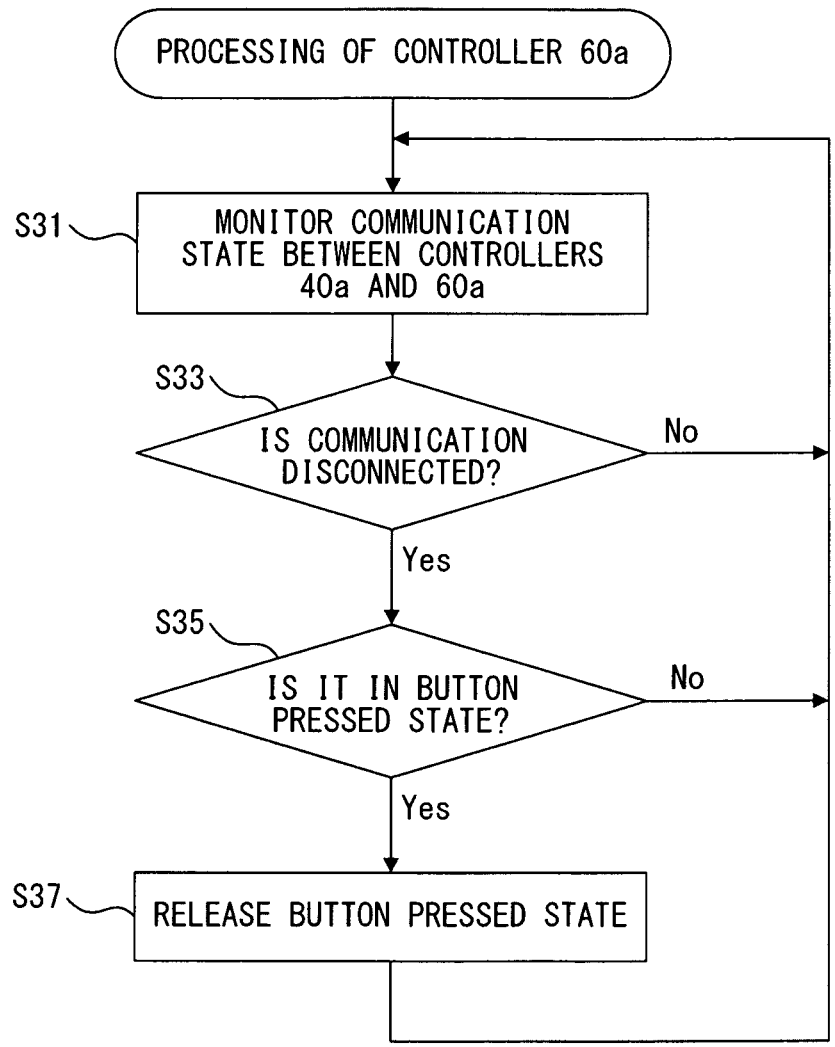
FIG. 9 is a flowchart which illustrates processing performed at a second controller according to embodiment 2 of the present invention.

A controller 60*a* according to the present embodiment executes processing illustrated in FIG. 9, in addition to control processing of peripheral equipment that is performed in accordance with an operation upon receiving an operation signal and processing illustrated in FIG. 4. That is to say, a controller 60*a* monitors a communication state between a controller 40*a* and a controller 60*a* through a control signal line L12 (step S31), and judges whether or not a communication state is a disconnection state (step S33). When a controller 60*a* judges that a communication state is a disconnection state, it further judges whether or not a state is a button pressed state (step S35). When a controller 60*a* judges that it is in a button pressed state, it stops a control which corresponds to pressing a button and releases a button pressed state (step S37). Then, it goes back to step S31 and monitors a communication state. Further, when a controller 60*a* judges that a communication state is normal or when it judges that a state is not a button pressed state, similarly, it goes back to step S31 and monitors a communication state.

Figure 10:
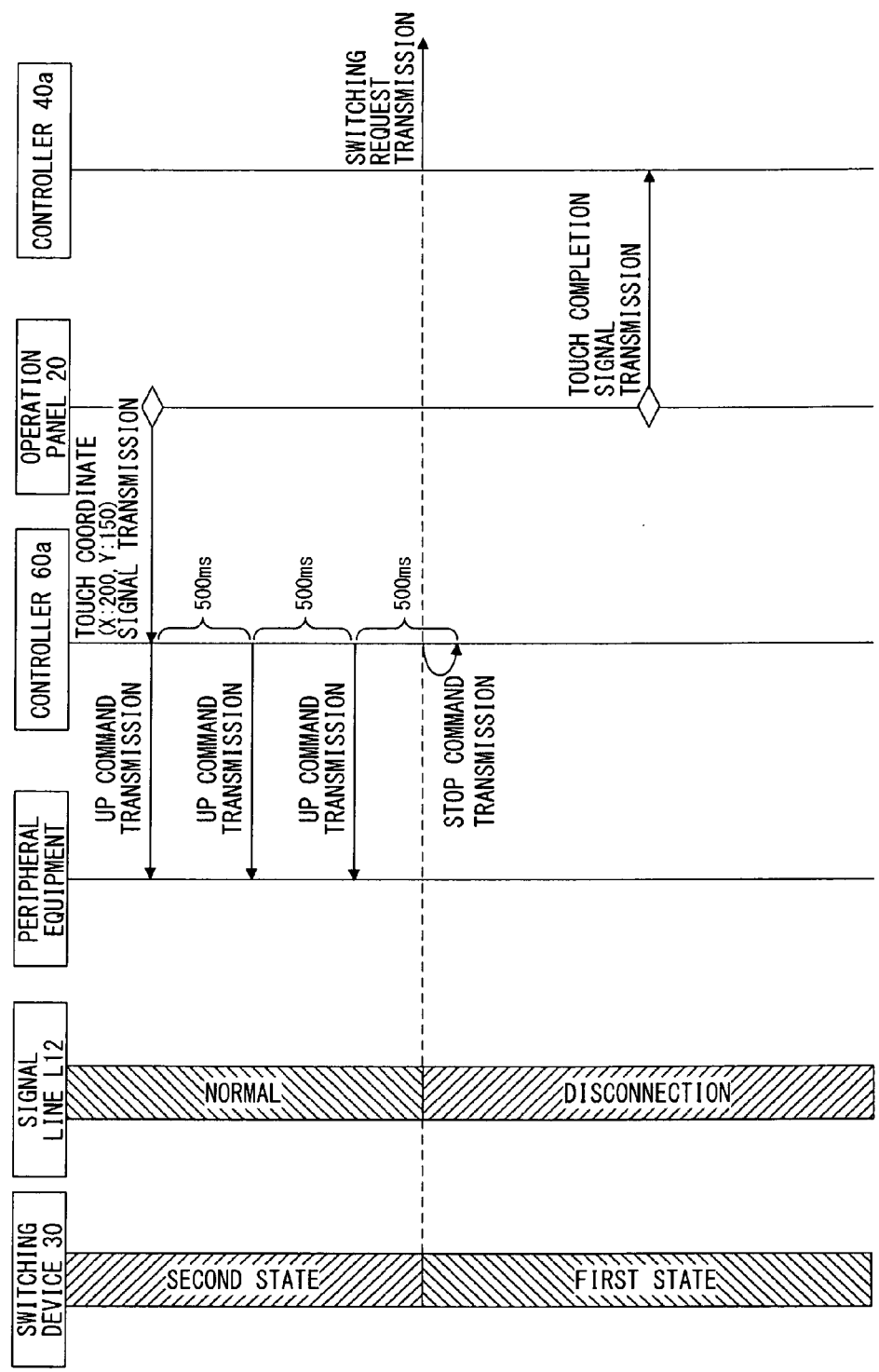
FIG. 10 is a sequential diagram which illustrates a flow of a signal between main components of a medical control system according to embodiment 2 of the present invention during a touch operation.

Hereafter, in reference to FIG. 10, explanations are given for an operation of a medical control system 100a, when a communication between a controller 40a and a controller 60a is disconnected during a touch operation in a second state. Such a communication disconnection may occur by a disconnection of a control signal line L12, a failure of a communication IF of a controller 40a or a controller 60a, or the like.

When a touch operation to an operation panel 20 is started in a second state, an operation panel 20 transmits, to a controller 60a, a touch signal which includes a touch coordinate. A controller 60a which has received a touch signal specifies a content of an operation by the touch coordinate and controls peripheral equipment in accordance with the content of the operation. For example, when a button to increase an output of an electric scalpel device 72 is displayed in a touch coordinate (X, Y)=(200, 150) included in a received touch signal, a controller 60a, upon receipt of the touch signal, transmits, on a regular basis (every 500 ms, for example) an UP command that instructs an electric scalpel device 72 to increase an output. After that, when a communication between a controller 40a and a controller 60a is disconnected by a disconnection of a control signal line L12, for example, a controller 60a detects that a communication state is a disconnection state due to the processing illustrated in FIG. 9 and stops transmitting an UP command. On the other hand, a controller 40a detects that a communication state is a disconnection state due to the processing illustrated in FIG. 8 and transmits, to a switching device 30, a switching request for switching a connection state to a first state. Finally, when a touch operation is completed in a first state, an operation panel 20 transmits a touch completion signal to a controller 40a.

As mentioned so far above, in a medical control system 100a according to the present embodiment, similarly to a medical control system 100 according to the first embodiment, since each controller monitors a connection state of a switching device 30, when a connection state of a switching device 30 is switched during a touch operation, a control which corresponds to a touch operation that is executed by a controller is released. In addition, since each controller monitors a communication state between controllers, a controller in which a communication is disconnected and which can no longer keep monitoring a connection state (a controller 60a in FIG. 7) releases a control which corresponds to a touch operation that is executed by the controller. Accordingly, a so-called sticking phenomenon can be prevented, and as a result of it, inconveniences which may occur due to a switching by a switching device 30 can be avoided.

Although in the present embodiment an example is illustrated in which a connection state is switched when a communication state between controllers enters into a disconnection state, a connection state is not necessarily switched. Even when an operation signal is transmitted to a controller which cannot monitor a connection state of a switching device 30 after a disconnection of a communication because a connection state is maintained, a control which corresponds to an operation signal is immediately released (for example, after transmitting an UP command only once, or the like), as long as the controller is capable of detecting the disconnection state. This is because no sticking phenomenon occurs for that.

Although the above mentioned embodiments have been described for the purposes of specific illustrations to facilitate an understanding of the invention, the present invention is not limited to these embodiments. Accordingly, various modifications and alterations may be made for a medical control system according to the present invention without deviating from the spirit and scope of the present invention as stipulated in claims.

What is claimed is:

1. A medical control system comprising:
  a first controller and a second controller, each being configured to control different peripheral equipment;
  a touch panel operation unit configured to receive an operation for processing by the first controller or the second controller; and
  a switching unit configured to selectively switch a connection state between: (i) a first state in which the first controller receives an operation from the touch panel operation unit, and (ii) a second state in which the second controller receives an operation from the touch panel operation unit; wherein:
  the touch panel operation unit has a touch signal transmission unit configured to transmit a touch signal to the first controller when the connection state is set to the first state and the touch panel operation unit is touched, and
  the first controller includes:
    a first operation command transmission unit configured to transmit an operation command on a relatively constant basis to the peripheral equipment, in which the operation command includes an operation content of the peripheral equipment specified by the received touch signal,
    a first connection state detection unit configured to monitor a control signal line connecting the switching unit and the first controller in order to detect a change of the connection state from the first state to the second state by the switching unit during a time period when the touch panel operation unit is touched, and
    a first control unit configured to stop the relatively constant transmission of the operation command in accordance with a detection result of the first connection state detection unit.

2. The medical control system according to claim 1, wherein
  the touch signal transmission unit transmits a touch signal to the second controller when the connection state is the second state and the touch panel operation unit is touched, and
  the second controller includes:
    a second operation command transmission unit configured to transmit an operation command on a relatively constant basis to the peripheral equipment, in which the operation command includes an operation content of the peripheral equipment specified by the received touch signal,
    a second connection state detection unit configured to monitor a control signal line connecting the switching unit and the first controller in order to detect a change of the connection state from the second state to the first state by the switching unit during a time period when the touch panel operation unit is touched, and
    a second control unit configured to stop the relatively constant transmission of the operation command in accordance with a detection result of the second connection state detection unit.

3. The medical control system according to claim 2, wherein the second controller is configured to detect a communication state between the first controller and the second controller, and to release a control which corresponds to an operation received by the touch panel operation unit in the second state when it detects that the communication state is a disconnection state.

4. The medical control system according to claim 1, wherein
- the touch panel operation unit is a touch panel display including a display unit and a touch panel sensor which are disposed so as to overlap with the display unit, and
- an operation received by the touch panel operation unit is a touch operation for a button which is displayed on the display unit.

5. The medical control system according to claim 1, wherein the touch signal transmission unit transmits to the second controller a touch completion signal when a touch operation is completed at the touch panel operation unit.

6. The medical control system according to claim 1, wherein the switching unit is configured separately from both the first controller and the second controller.

* * * * *